United States Patent [19]

Grimes

[11] 4,416,273

[45] Nov. 22, 1983

[54] CONNECTOR VALVE ASSEMBLY FOR ENDOTRACHEAL TUBES

[76] Inventor: Jerry L. Grimes, 1798 N. Garey Ave., Pomona, Calif. 91767

[21] Appl. No.: 273,662

[22] Filed: Jun. 15, 1981

[51] Int. Cl.³ .............................................. A61M 16/00
[52] U.S. Cl. ......................... 128/207.16; 128/207.15; 128/912; 604/283
[58] Field of Search ...................... 128/207.14, 207.15, 128/207.16, 350 R, 350 V, 912, 1 B, 30; 604/167, 169, 256, 283

[56] References Cited

U.S. PATENT DOCUMENTS

| | | | |
|---|---|---|---|
| 2,708,927 | 5/1955 | Dixon et al. ......................... | 128/1 B |
| 3,461,877 | 8/1969 | Morch ............................. | 128/207.14 |
| 3,902,500 | 9/1975 | Dryden ........................... | 128/207.14 |
| 4,240,417 | 12/1980 | Holever . | |

FOREIGN PATENT DOCUMENTS

| | | | |
|---|---|---|---|
| 1296652 | 5/1962 | France ............................. | 128/207.16 |
| 2359615 | 3/1978 | France ............................. | 128/207.14 |
| 2019219 | 10/1979 | United Kingdom ................ | 604/256 |

OTHER PUBLICATIONS

*Special New Low Resistance to Flow Tube and Endotracheal Tube Adapter for Use During Fiberoptic Bronchoscopy;* Carden et al., Sep.–Oct., 1975, pp. 1-4.
Article A—Unidentified Tracheal Tube Connector.
Article B—Tracheal Tube Connector Marked "Portex".
Article C—Tracheal Tube Connector Marked "Shirley Labs. Pat. Pending".

*Primary Examiner*—Henry J. Recla
*Assistant Examiner*—Karin M. Reichle
*Attorney, Agent, or Firm*—Litman, Day & McMahon

[57] ABSTRACT

A connector valve assembly for admission of catheters through endotracheal tubes employs a connector body having a tracheal tube port, a respiratory tube port and an end portion adapted for insertion of a catheter through the body and through the tracheal tube for patient airway suctioning. An end cap on the end portion has an aperture with a ring seal for sealably engaging the catheter as it is inserted therethrough and has a check valve disposed inwardly of the ring seal toward the respiratory and tracheal tube ports. The end cap defines an air lock chamber for insertion of the catheter through the connector body without interrupting positive pressure ventilation of the patient.

2 Claims, 3 Drawing Figures

CONNECTOR VALVE ASSEMBLY FOR ENDOTRACHEAL TUBES

This invention relates to medical tube connector devices and, in particular, to a connector assembly for endotracheal tubes utilizing a valve to limit air movement.

BACKGROUND OF THE INVENTION

During continuous mechanical ventilation of patients, a common clinical practice involves the use of positive end expiratory pressure (PEEP) wherein the ventilator provides a specific amount of pressure measured in centimeters of water pressure during the expiratory phase of ventilation. This "pressure breathing" tends to ventilate the entire lung system of the patient and to assist breathing of those with injuries or debilitating illnesses having labored or otherwise breathing difficulties. The slight positive pressure of the incoming air or gas to assist inhalation must be overcome during expiration and suitable valves and pressure regulators are emplaced in the ventilator to provide for expiration.

During positive end expiratory pressure breathing, it is desirable not to interrupt the established routine of breathing during ventilation; however, virtually all patients on mechanical ventilation systems require frequent suctioning of the airways and lung organs to maintain proper bronchial hygiene to prevent even more serious illnesses such as bronchial pneumonia.

Currently, when suctioning is required, the patient must be physically disconnected from the mechanical ventilation device because previous systems and connector devices have not permitted administering personnel to simultaneously maintain the pressurized system and suction through a catheter.

In another common clinical procedure, an examination instrument known as a bronchofiberscope is inserted through the connector assembly and through the tracheal tube for visual inspection of the patient's lungs and bronchial passages. This inspection is often hampered because the patient is on pressurized mechanical ventilation and disconnection from the ventilator is ordinarily required prior to insertion of the bronchofiberscope.

OBJECTS OF THE INVENTION

The objects of the present invention are: to provide a connector valve assembly for maintaining positive end expiratory pressure in patients connected to a positive pressure ventilation system; to provide such a connector valve assembly in which a catheter or other small diameter tubular device can be inserted through a connector body and tracheal tube without loss of air pressure therein; to provide a connector valve assembly having a valve means including a ring seal and a one-way check valve therein cooperating to seal the connector body yet admit catheters and the like; to provide such a connector valve assembly having an air lock chamber between a ring seal and a check valve to maintain positive pressure within the connector body and tracheal tube; to provide such a connector valve assembly having a cap arrangement connectable thereto and defining an air lock chamber with a ring seal at one end and a check valve at another end portion, said cap arrangement being readily connectable to standard connector bodies; and to provide such a connector valve assembly which is sturdy and reliable in use, contains few moving parts, and is inexpensive to manufacture.

Other objects and advantages of this invention will become apparent from the following description taken in connection with the accompanying drawings wherein are set forth, by way of illustration and example, certain embodiments of this invention.

DETAILED DESCRIPTION OF THE PREFERRED EMBODIMENT

Figure 1:
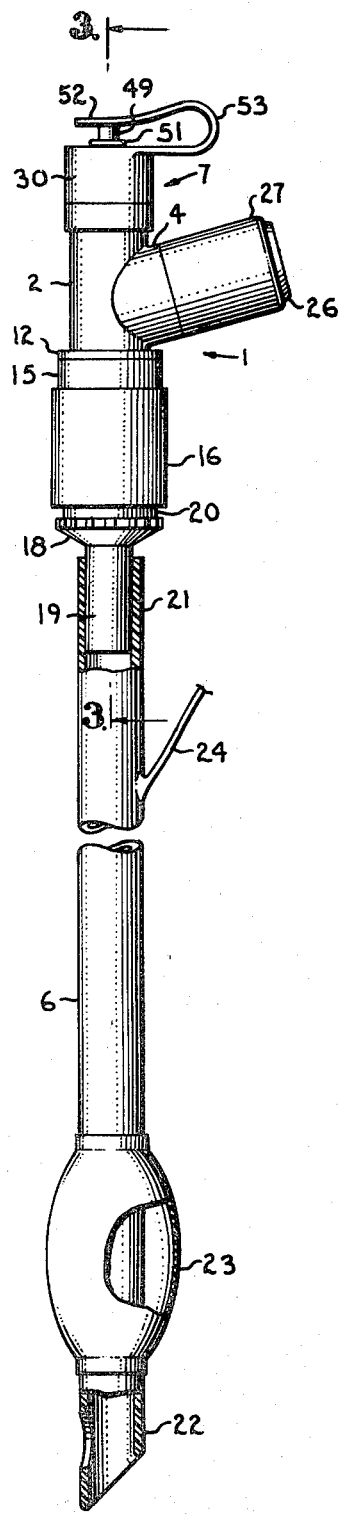
FIG. 1 is a side elevational view of the connector valve assembly shown joined to an endotracheal tube.

As required, a detailed embodiment of the present invention is disclosed herein, however, it is to be understood that the disclosed embodiment is merely exemplary of the invention which may be embodied in various forms. Therefore, specific structural and functional details disclosed herein are not to be interpreted as limiting, but merely as the basis for the claims and as a representative basis for teaching one skilled in the art to variously employ the present invention in virtually any appropriately detailed structure.

Referring to the drawings in more detail:

The reference numeral 1 generally indicates a connector valve assembly for admission of catheters and the like through endotracheal tubes and having a connector body 2 with a tracheal tube port 3, a respiratory tube port 4 and an open end portion 5 for insertion of a catheter through the body 2 and through a tracheal tube 6.

A valve means 7 at the open end portion 5 opens and sealably engages the catheter and a check valve inwardly thereof opens to the valve body interior for insertion of the catheter into the body without opening the body to the outside atmosphere and causing loss of positive system pressure.

In the illustrated example, the connector body 2 is substantially standard in configuration and comprises an elongate, tubular member having an outer wall 9 and an inner wall 10 defining a through bore. The illustrated tracheal tube port 3 is situated at the bottom of the body 2 and has spaced upper and lower flanges 12 and 13 with the lower flange 13 having a sloping surface 14 for snap fitting of an engagement ring portion 15 of a swivel adaptor 16.

The tracheal tube coupling 18 has a lower insert end 19 and an upper reduction couple 20 insertable into the open end portion of the swivel adaptor 16. The exemplary reduction couple 20 may have an industry standard 15 mm. outside diameter with a one degree taper for a tight press fit.

The endotracheal tube 6 has an upper connection end 21 and a lower, gas outlet end 22 associated with an expansible bladder or cuff 23 which is inflatable by means of an air line 24.

The respiratory tube port 4 joins the connector body 2 at a substantially angular relationship and has a passage therethrough (not shown) communicating with the through bore of the body tube for administering a gas, such as air or oxygen, through the tracheal tube 6 and into the patient's lungs. The respiratory tube port 4 has an end flange 26 and may be plain or include a swivel connector 27.

The respiratory tube port 4 connects to a respiratory tube (not shown) which is in turn connected to a mechanical ventilator including an air or gas pump to provide a source of pressurized air for administration to a patient. This procedure, known as positive end expiratory pressure (PEEP) involves pressure breathing or reversal of ordinary breathing functions wherein the patient relaxes and the incoming pressurized air expands the diaphragm and causes the lungs to fill with the gas. Expiration is accomplished by positive contraction of the diaphragm sufficient to overcome the incoming air pressure and permit expiration. Normally the mechanical ventilating device (not shown) includes valves, regulators and the like.

Patients on mechanical ventilation normally require frequent airway suctioning as through a suction catheter 29 to maintain the proper bronchial hygiene. Alternatively, examining instruments such as a bronchofiberscope (not shown) may be passed down the airway for visual examination of the patient's airway and lungs. Both the catheter and bronchofiberscope are long, slender, tubular devices and are commonly inserted through the endotracheal tube connector and endotracheal tube 6 when emplaced. Particular problems are encountered with the positioning of the suction catheter 29 when the ventilation device provides pressurized air because entry of the catheter into the tube connector has heretofore caused positive pressure to be lost and the patient's blood oxygen supply to decrease drastically.

Using the present invention, positive system pressure is not lost upon the insertion of the catheter 29 or bronchofiberscope through the connector body 2 and into the tracheal tube 6. In the illustrated example, the valve means 7 is associated with a cap arrangement 30 having an end wall 31 and a surrounding side wall 32. The cap arrangement 30 has a lower section 33 joined thereto, also with a surrounding side wall 34 and having an inwardly directed flange providing an inner shoulder 35 which acts as a valve seat as described below. The side wall 34 forms a skirt sized to fit securely over the open end portion 5 and includes the valve means 7 as an assembly therewith. An end shoulder 36 confronts the inner shoulder 35 and a one-way check valve 38 is captured therebetween.

In the illustrated example, the check valve 38 has a disc member 39 with a peripheral edge 40 and a central aperture portion 41. A flexible, rubbery valve flapper 42 is secured at one portion to the disc member 39 and has a flapper periphery overlying a portion of the inner shoulder 35 when thereagainst, whereby the inner shoulder 35 acts as a valve seat for the flapper 42. The positioning of the check valve 38 permits the flapper 42 to swing open when the catheter 29 is routed through the connector body 2 and to swing closed to a sealed position immediately upon withdrawal of the catheter 29 and held against the valve seat by greater than atmospheric or positive pressure.

Figure 3:
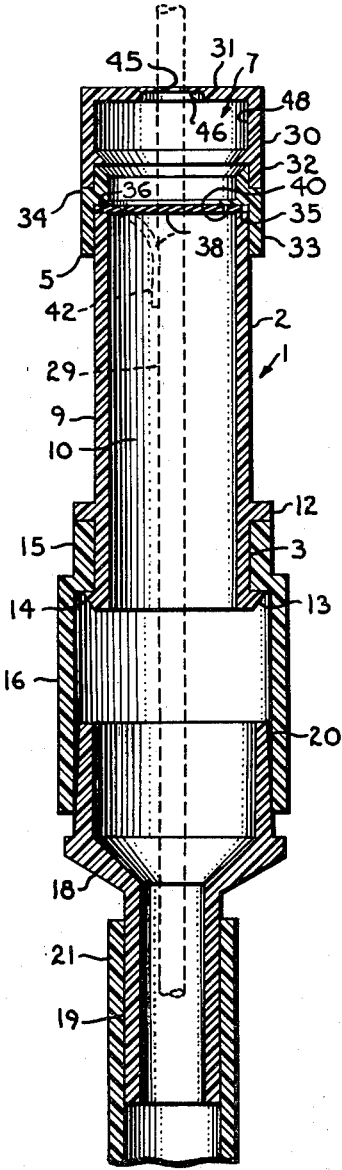
FIG. 3 is a longitudinal sectional view taken along lines 3—3, FIG. 1.
Figure 2:
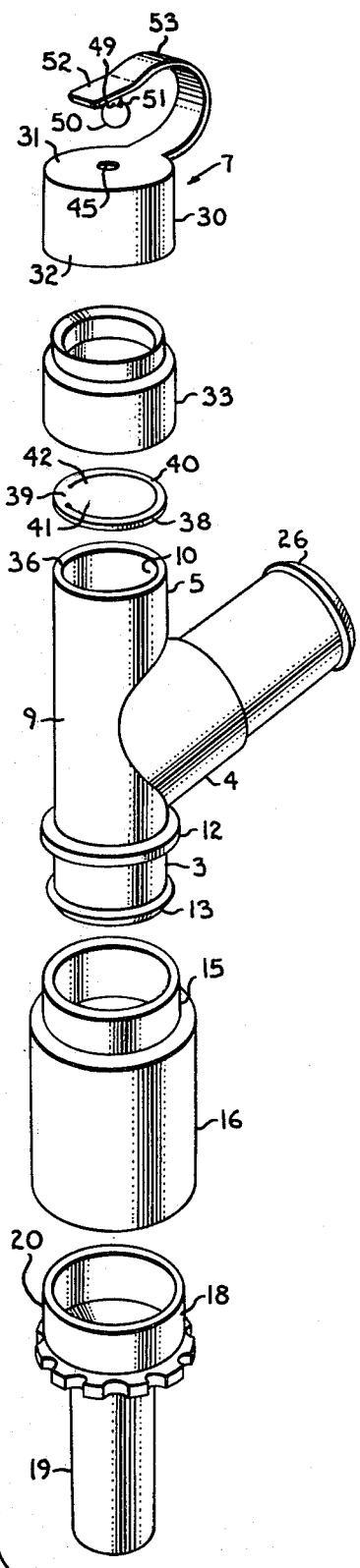
FIG. 2 is a disassembled, perspective view of the connector valve assembly.

An aperture 45 extends axially through the end wall 31 and has a ring seal portion 46 formed therewith having an inside diameter sized for sealing engagement with the outside surface of the catheter 29. The ring seal portion 46 may be integral with the end wall 31 or may be a separate emplaced O-ring or the like suitably mounted within the end wall 31, as long as the ring seal portion 46 sealably engages the catheter wall and prevents loss of positive pressure air through the aperture 45. The side walls 32 and 33 generally define an air lock chamber for 48, FIG. 3, located between the first seal, the ring seal portion 46 and the second seal or check valve 38. A removable plug 49 comprises a shaft-mounted ball 50 with an encircling seal flange 51 and secured to an upper tab portion 52 joined to a tether 53 connected, as by molding, to end wall 31. The plug 49 is selectively insertable into the aperture 45 to close the air lock chamber 48 and removable therefrom to route the catheter 29 into the connector body 2.

In use, the plug 49 is removed and the end of the catheter 29 inserted through the aperture 45 with the ring seal portion 46 sealing therearound. The catheter 29 is pushed quickly through the air lock chamber 48 and the check valve 38 and into the connector body 2. The catheter 29, bronchofiberscope or other similar device is then manipulated as desired by the doctor or health specialist to perform the necessary suctioning, inspection or the like.

Upon completion of the suctioning or inspection, the catheter 29 is pulled outwardly of the tracheal tube 6 and connector body 2 whereupon the check valve 38 is no longer held open and the positive pressure within the connector body 2 administered by the mechanical ventilator pushes the flapper 42 to seal off the air lock member 48. The catheter 29 is then removed the remainder of the way through the aperture 45 and the plug 49 fitted thereto upon completion.

Throughout this entire procedure, the connector body 2 remains closed and no noticeable amount of air escapes to cause a drop in the positive pressure.

It is to be understood that while one form of this invention has been illustrated and described, it is not to be limited to the specific form or arrangement of the parts herein described and shown, except insofar as such limitations are included in the following claims.

What is claimed and desired to secure by Letters Patent is:

1. A connector valve assembly for admission of catheters through endotracheal tubes comprising:
    (a) a connector body having a tracheal tube port, a respiratory tube port and an open end portion for insertion of a catheter through said body and said tracheal tube;
    (b) a valve means at said open end portion including a ring seal portion for sealably engaging said catheter and a check valve disposed inwardly of said ring seal portion toward said respiratory tube port and said tracheal tube port;
    (c) wall means defining an air lock chamber between said ring seal portion and said check valve for insertion of a catheter without opening said connector body to the outside atmosphere;
    (d) said wall means includes an end wall with said ring seal portion extending therethrough and a surrounding side wall having a lower skirt portion sized to fit over said open end portion;
    (e) said open end portion having a shoulder; said skirt portion having an inwardly directed flange providing an inner shoulder to confront said shoulder; and
    (f) a disc member having a peripheral edge captured between said shoulder and said inwardly directed flange and having portions providing a valve seat wherein said check valve has a flapper attached to said disc member and sealably engaging said valve seat.

2. The connector valve set forth in claim 1 wherein:
    (a) said tracheal tube port and said respiratory tube port each have a sleeve fitted thereon for swiveling connection of said connector body with tracheal and respiratory tubes.

* * * * *